United States Patent [19]

Wachtendorf et al.

[11] Patent Number: 5,703,268

[45] Date of Patent: Dec. 30, 1997

[54] ACRYLONITRILE RECOVERY PROCESS

[75] Inventors: Paul Trigg Wachtendorf, Wapakoneta; Sanjay Parushottam Godbole, Solon; Jeffrey Earle Rinker, Elida, all of Ohio

[73] Assignee: The Standard Oil Company, Cleveland, Ohio

[21] Appl. No.: 629,129

[22] Filed: Apr. 8, 1996

[51] Int. Cl.$^6$ .................................................. C07C 255/08
[52] U.S. Cl. ........................................................ 558/466
[58] Field of Search .............................................. 558/466

[56] References Cited

U.S. PATENT DOCUMENTS 3,885,928   5/1975   Wu .
,234,510   11/1980   Wu .

*Primary Examiner*—Robert Gerstl
*Attorney, Agent, or Firm*—Michael F. Esposito; David J. Untener

[57] ABSTRACT

A process for the recovery of acrylonitrile or methacrylonitrile obtained from the reactor effluent of an ammoxidation reaction of propylene or isobutylene comprising passing the reactor effluent through an absorber column and recovery column and stripper column wherein the improvement comprises increasing the recovery column top pressure by mechanical means by about 0.1 to 5 psi to improve the hydraulic capacity of the recovery and stripper columns.

8 Claims, No Drawings

ACRYLONITRILE RECOVERY PROCESS

BACKGROUND OF THE INVENTION

Field of the Invention

The present invention is directed to an improved process for the manufacture of acrylonitrile or methacrylonitrile. In particular, the present invention is directed to the improvement in the recovery procedures utilized during the manufacture of acrylonitrile and methacrylonitrile.

Recovery of acrylonitrile/methacrylonitrile produced by the ammoxidation of propylene or isobutylene on a commercial scale has been accomplished by quenching the reactor effluent with water followed by passing the gaseous stream containing acrylonitrile or methacrylonitrile resulting from the quench to an absorber where water and the gases are contacted in counter-current flow to remove substantially all the acrylonitrile or methacrylonitrile, the aqueous stream containing substantially all the acrylonitrile or methacrylonitrile is then passed through a series of distillation columns and associated decanters for separation and purification of product acrylonitrile or methacrylonitrile.

Typical recovery and purification systems that are used during the manufacture of acrylonitrile or methacrylonitrile are disclosed in U.S. Pat. Nos. 4,234,510 and 3,885,928, assigned to the assignee of the present invention and herein incorporated by reference.

SUMMARY OF THE INVENTION

It is the primary object of the present invention to provide an improved process for the manufacture of acrylonitrile or methacrylonitrile.

It is another object of the present invention to provide an improved recovery and purification procedure for utilization during the manufacture of acrylonitrile or methacrylonitrile.

It is a further object of the present invention to provide an improved process for the manufacture of acrylonitrile or methacrylonitrile which reduces waste gas and improves the product throughput, recovery efficiency and product quality by reducing the amount of organic impurities in the resultant final product.

Additional objects, advantages and novel features of the invention will be set forth in part in the description which follows, and in part, will become apparent to those skilled in the art upon examination of the following or may be learned by the practice of the invention. The objects and advantages of the invention may be realized and obtained by means of the instrumentalities and combinations particularly pointed out in the appended claims.

To achieve the foregoing and other objects and in accordance with the purpose of the present invention as embodied and broadly described herein, the process of the present invention comprises transporting the reactor effluent obtained during the ammoxidation of propylene or isobutylene to a quench column wherein the hot effluent gases are cooled by contact with an aqueous spray, the cooled reactor effluent is then passed overhead to an absorber column wherein the acrylonitrile or methacrylonitrile is absorbed in water, the aqueous solution containing the acrylonitrile or methacrylonitrile is then passed through a recovery distillation column and stripper distillation column to recover the acrylonitrile or methacrylonitrile product wherein the improvement comprises increasing the recovery distillation column top pressure by mechanical means by about 0.1 to 5 psi to improve the hydraulic capacity of the recovery and stripper columns. For example, typically the recovery column top pressure in the recovery and purification section of an acrylonitrile plant is designed to run at between about 1 to less than 5 psig. The present invention is directed to mechanically, for example by the addition of a pressure valve, increasing the top pressure of the recovery column above the designed pressure by between 0.1 to 5 psi, preferably 0.25-0.5 to 5.0, especially preferred being 1.0 to 5.0 psi.

In a preferred embodiment of the present invention, the recovery column top pressure is maintained at between 5 to 10 psig, preferably greater than 5 to 10 psig, especially preferred being 5.5 to 7.5 psig.

In a preferred embodiment of the present invention, the process is performed with the reactor effluent obtained from the ammoxidation of propylene, ammonia and oxygen to produce acrylonitrile.

In a still preferred embodiment of the present invention, the reactor effluent is obtained by the reaction of propylene, ammonia and air in a fluid bed reactor while in contact with a fluid bed catalyst.

Conventional fluid bed ammoxidation catalyst may be utilized in the practice of the invention. For example, fluid bed catalyst as described in U.S. Pat. Nos. 3,642,930 and 5,093,299, herein incorporated by reference, may be utilized in the practice of the present invention.

In conventional recovery and purification procedures for the recovery of acrylonitrile or methacrylonitrile, it has been found that jet flooding in the recovery and stripper columns typically sets the maximum amount of lean water which can be circulated through the absorber, recovery and stripper columns. The present invention allows the operation of the recovery and stripper columns at increased pressure, thus increasing the throughput at which jet flooding occurs, thereby allowing for an increase in the rate of reactor operation and lower absorber off-gas losses. This is accomplished by increasing the flow of the lean water from the recovery and stripper columns to the absorber with the surprising discovery that the total recovery procedure does not lose any operating efficiency. The practice of the invention allows for higher reaction production rates while maintaining the minimum requirements as to the lean water to product ratio (at least 11:1). The practice of the present invention is very beneficial when utilized in combination with a recovery and purification procedure which operates at a lean water to product ratio of 12:1 to 11:1 in the absorber column.

DETAILED DESCRIPTION OF THE INVENTION

The present invention will now be described in detail. The reactor effluent obtained by the ammoxidation of propylene or isobutylene, ammonia and oxygen containing gas in a fluid bed reactor while in contact with a fluid bed ammoxidation catalyst is transported to a quench column wherein the hot effluent gases are cooled by contact with water spray. Typically, any excess ammonia contained in the effluent is neutralized by contact with sulfuric acid in the quench to remove the ammonia as ammonium sulfate. The cooled effluent gas containing the desired product (acrylonitrile or methacrylonitrile and HCN) is then passed into the bottom of an absorber column wherein the products are absorbed in water which enters the column from the top. The nonabsorbed gases pass from the absorber through a pipe located at the top of the absorber. The aqueous stream containing the desired product is then passed from the absorber bottom to the upper portion of a first distillation column (recovery column) for further product purification. The product recovered from the upper portion of the recovery column is then sent to a second distillation column for further purification and recovery of product acrylonitrile or methacrylonitrile. The bottom stream obtained from the recovery column is sent to a stripper distillation column to recover crude acetonitrile which is a valuable coproduct.

In the practice of the present invention an automatic pressure control valve is installed in the recovery column overhead line to enable the top pressure of the recovery column to be increased by about 0.1 to 5 psi above the design top recovery column pressure. Typically, the recovery column top pressure is between 1 to less than 5 psig, normally between 4 to 4.5 psig. In the preferred practice of the present invention, the recovery column top pressure is operated at a constant pressure which may vary from 5 psig to about 10 psig, preferably 5.5 to 7.5 psig. The improvement of the present invention is applicable to separate recovery and stripper tower designs as well as stacked recovery/stripper tower designs for the recovery of acrylonitrile or methacrylonitrile provided that tower hydraulics is limited by jet flooding. The pressure control valve employed may be obtained from any control valve manufacturer. It may be automatically actuated or manually controlled.

Preferably, the ammoxidation reaction is performed in a fluid bed reactor although other types of reactors such as transport line reactors are envisioned. Fluid bed reactors, for the manufacture of acrylonitrile are well known in the prior art. For example, the reactor design set forth in U.S. Pat. No. 3,230,246, herein incorporated by reference, is suitable.

Conditions for the ammoxidation reaction to occur are also well known in the prior art as evidenced by U.S. Pat. Nos. 5,093,299; 4,863,891; 4,767,878 and 4,503,001; herein incorporated by reference. Typically, the ammoxidation process is performed by contacting propylene or isobutylene in the presence of ammonia and oxygen with a fluid bed catalyst at an elevated temperature to produce the acrylonitrile or methacrylonitrile. Any source of oxygen may be employed. For economic reasons, however, it is preferred to use air. The typical molar ratio of the oxygen to olefin in the feed should range from 0.5:1 to 4:1, preferably from 1:1 to 3:1. The molar ratio of ammonia to olefin in the feed in the reaction may vary from between 0.5:1 to 5:1. There is really no upper limit for the ammonia-olefin ratio, but there is generally no reason to exceed a ratio of 5:1 for economic reasons.

The reaction is carried out at a temperature of between the ranges of about 260° to 600° C., but the preferred ranges being 310° to 500° C., especially preferred being 350° to 480° C. The contact time, although not critical, is generally in the range of 0.1 to 50 seconds, with preference being to a contact time of 1 to 15 seconds.

In addition to the catalyst of U.S. Pat. No. 3,642,930, other catalysts suitable for the practice of the present invention are set forth in U.S. Pat. No. 5,093,299, herein incorporated by reference.

The conditions under which the absorber column, recovery column and stripper column are maintained range between 5 to 7 psig (80° F. to 110° F.), 1 to 4.5 psig (155° F. to 170° F.), and 7 to 13 psig (170° F. to 210° F.), respectively.

The improvement of the present invention is distinguished over the prior art by operating the recovery column by mechanical adjustment at a pressure which is above its normal designed pressure during the practice of the ammoxidation process for the manufacture of acrylonitrile/methacrylonitrile. Conventional procedures utilized a recovery column top pressure of less than 5 psig. In the preferred practice of the present invention, the recovery column top pressure is typically operated at a pressure ranging from 5 to 10 psig, preferably between 5.5 to 7.0 psig.

Operation of the recovery and purification process of the present invention results in the ability to achieve high throughput rates through the reactor without making any modifications to the recovery and purification system which involve capital expenditures. The present invention not only results in an unexpected improvement in the production rates but achieves this improvement without increasing the size of the towers utilized in the recovery and purification section. In addition, the attendant increase in production rates does not come with any observed deterioration in the performance of the absorber column during the recovery or the acrylonitrile or methacrylonitrile. The present invention results in improved efficiency of operation, improved throughput, increased productivity without the necessity of expenditure of capital.

As will be evident to those skilled in the art, various modifications of this invention can be made or followed in light of the foregoing disclosure and discussion without departing from the spirit and scope of the disclosure or from the scope of the claims.

What is claimed is:

1. A process for the recovery of acrylonitrile or methacrylonitrile obtained from the reactor effluent of an ammoxidation reaction of propylene or isobutylene comprising passing the reactor effluent through an absorber column, a recovery column operating at a first top pressure of no greater than 5 psig and fitted with an overhead line to remove product acrylonitrile or methacrylonitrile for further purification and recovery and a stripper column wherein the improvement comprises placing a pressure control means on the overhead line and adjusting the pressure control means to increase the first top pressure to a second top pressure which is between about 0.1 to 5 psi greater than the first top pressure to improve the hydraulic capacity of the recovery and stripper columns.

2. The process of claim 1 wherein the reactor effluent is obtained from the reaction of propylene, ammonia and an oxygen containing gas in a fluid bed reactor which is in contact with a fluid bed ammoxidation catalyst.

3. The process of claim 1 wherein the reactor effluent is obtained from the reaction of isobutylene, ammonia and an oxygen containing gas in a fluid bed reactor while in contact with a fluid bed ammoxidation catalyst.

4. The process of claim 1 wherein the recovery column is maintained at a second top pressure of between about 5 to about 10 psig.

5. The process of claim 1 wherein the recovery column second top pressure is maintained between about 5.5 to about 7.0 psig.

6. The process of claim 1 wherein the recovery column first top pressure is increased by between about 0.25 to about 5 psi.

7. The process of claim 1 wherein the recovery column first top pressure is increased by between about 0.5 to about 5 psi.

8. The process of claim 1 wherein the recovery column first top pressure is increased by between about 1.0 to about 5 psi.

* * * * *